US010058328B2

(12) United States Patent
Dalle et al.

(10) Patent No.: US 10,058,328 B2
(45) Date of Patent: Aug. 28, 2018

(54) ANASTOMOTIC DEVICE FOR JOINING LUMENS OR VISCERA TO EACH OTHER (71) Applicants: COUSIN BIOTECH, Wervicq Sud (FR); UNIVERSITE DE DROIT ET DE LA SANTE DE LILLE 2, Lille (FR)

(72) Inventors: Valéry Dalle, Croix (FR); Gilles Solecki, Lannoy (FR); François Pattou, Lille (FR); Jacques Himpens, Vinderhoute (BE); Robert Caiazzo, Lille (FR)

(73) Assignees: COUSIN BIOTECH, Wervicq Sud (FR); UNIVERSITE DE LILLE, Lille (FR)

( * ) Notice: Subject to any disclaimer, the term of this patent is extended or adjusted under 35 U.S.C. 154(b) by 64 days.

(21) Appl. No.: 14/909,147

(22) PCT Filed: Jul. 9, 2014

(86) PCT No.: PCT/FR2014/051755
§ 371 (c)(1),
(2) Date: Feb. 1, 2016

(87) PCT Pub. No.: WO2015/015080
PCT Pub. Date: Feb. 5, 2015

(65) Prior Publication Data
US 2016/0174987 A1 Jun. 23, 2016

(30) Foreign Application Priority Data
Aug. 1, 2013 (FR) ...................................... 13 57621

(51) Int. Cl.
A61B 17/08 (2006.01)
A61B 17/11 (2006.01)

(52) U.S. Cl.
CPC ... *A61B 17/1114* (2013.01); *A61B 2017/1139* (2013.01)

(58) Field of Classification Search
CPC ......... A61B 17/1114; A61B 2017/1103; A61B 2017/1107; A61B 2017/1132; A61B 2017/1135; A61B 2017/1139
(Continued)

(56) References Cited

U.S. PATENT DOCUMENTS 5,941,908 A   8/1999   Goldsteen
6,527,800 B1  3/2003   McGuckin
(Continued)

FOREIGN PATENT DOCUMENTS

DE      10325128 A1     1/2005
FR       2976782 A1    12/2012
WO    20120175847 A1   12/2012

OTHER PUBLICATIONS

PCT Preliminary Search Report and Written Opinion dated Feb. 11, 2016, for PCT Application No. PCT/FR2014/051755, pp. 1-10 including translation.

*Primary Examiner* — Melanie Tyson
(74) *Attorney, Agent, or Firm* — MH2 Technology Law Group, LLP (57) ABSTRACT An anastomosis device for joining hollow lumens or viscera, suitable for deployment at the surface of two superposed adjacent lumens. The device has a main tubular body of longitudinal axis (L), having first and second open ends and opposite outside and inside faces. The main tubular body has at least three columns of loops and at least three rows of loops and sets of proximal and distal radial projections extending along at least a depth (E) at the peripheries of the first and second ends respectively. The distal and proximal sets are spaced apart by a minimum internal distance (D), and further include a set of intermediate radial projections (Continued)

extending along at most a depth (e) and arranged between the sets of proximal and distal radial projections. The depth (e) is less than (E), and the minimum internal distance (D) is determined so as to receive two superposed adjacent lumens.

19 Claims, 5 Drawing Sheets

(58) Field of Classification Search
USPC .................................................. 606/153–156
See application file for complete search history.

(56) References Cited

U.S. PATENT DOCUMENTS

| | | |
|---|---|---|
| 6,695,878 B2 * | 2/2004 | McGuckin, Jr. .......................... A61B 17/12109 606/153 |
| 2002/0082614 A1 | 6/2002 | Logan |
| 2003/0032967 A1 | 2/2003 | Park |
| 2007/0123917 A1 | 5/2007 | Ortiz |
| 2011/0264186 A1 | 10/2011 | Berglung |

* cited by examiner

ANASTOMOTIC DEVICE FOR JOINING LUMENS OR VISCERA TO EACH OTHER

BACKGROUND OF THE INVENTION

The present invention relates to the technical field of anastomosis devices for joining together hollow lumens or viscera, the devices being suitable for being deployed at the surfaces of superposed adjacent lumens.

Surgical anastomosis is surgically butt joining two ducts by manual suturing or by stapling. Suturing is performed with thread that is referred to as resorbable since it disappears by itself over time inside the organism. Such sutures are used in digestive surgery (relating to surgery on the stomach, the duodenum, the small intestine, the colon, or the anus), and in bariatric surgery, and also in urological surgery with regard to the urinary tract. Sometimes, surgical anastomoses are performed using a non-resorbable suture, in particular for anastomosis of blood vessels, in particular of the arteries.

Anastomosis in the field of digestive surgery is used to re-establish continuity of the digestive tube. The digestive tube, made up of the duodenum, the small intestine, and the colon, may become blocked by a neoplasm. It is thus necessary to re-establish the flow of food by resecting the blocked portion of the digestive tube, and then butt joining the two free ends of the digestive tube. Such butt joining is achieved by means of a circular stapler, or manually by sutures.

The purpose of anastomosis in the field of bariatric surgery is for surgically treating obesity. One of the surgical techniques is biliopancreatic diversion or the Scopinaro operation. That surgical technique consists in particular in making a pouch by removing a large portion of the stomach, and by connecting it, via an anastomosis, to the last portion of the small intestine, thus taking the major portion of the intestine out of circuit. Consumed food is thus digested only very little.

Various types of digestive anastomoses are as follows:
  an eso-gastric anastomosis is performed between the esophagus and the stomach;
  a gastro-jejunal anastomosis is performed between the stomach and the jejunum;
  a duodeno-jejunal anastomosis is performed between the duodenum and the jejunum;
  an ileocolic anastomosis is performed between the ileun and the colon;
  a colo-colic anastomosis is performed between two portions of the colon; and
  an ileo-rectal anastomosis is performed between the ileun and the rectum.

Implantable devices making it possible to form gastrointestinal anastomoses via the transesophageal endoscopic approach initially lead to ischemic necrosis of the tissues by compression, which necrotic portion then falls into the small intestine after maturation of the necrosis. Maturation of the necrosis may be defined as the moment from which the necrotic tissues may be separated easily from the vascularized tissues.

Documents EP 1 790 297 A1 and WO 03/000142 disclose anastomosis devices comprising a tube constituted by shape-memory wires that, as can be seen in the structure shown in FIG. 2 of WO 03/000142 and in FIG. 8 of EP 1 790 297 A1, are interwoven and shaped either by braiding, or manually by interweaving the wires on a support including nails.

In operation, the devices of annular shape, as can be seen for example in FIG. 5C of EP 1 790 297 A1, or in FIG. 3B of WO 03/000142, present petals that are interwoven and that project along their outer periphery.

The gastric and intestinal tissues positioned between the petals necrotize by compression, then the necrotic portion, together with the device, falls into the digestive system so as to leave in place an opening, commonly referred to as an anastomosis.

Just after being implanted and before the tissues have healed, the devices may slide from their implantation site in such a manner that physical connection between the stomach and the small intestine is thus no longer guaranteed. Gastric and intestinal secretions then flow into the peritoneal cavity. The patient may then die of peritonitis or of a general infection (septicemia).

After several months of implantation and following necrosis of the tissues that are superposed and positioned between the petals, the devices are designed to fall into the small intestine. As a result, they are potentially dangerous for the patient. Specifically, once they have fallen into the small intestine, the devices may block the digestive system, generating an occlusion of the intestinal duct and then causing an intestinal perforation.

Furthermore, gastric acid can corrode the titanium-nickel alloys used in the devices and cause wires to break at multiple locations, after an implantation duration that is longer than 120 days. The sharp ends of the broken wires may perforate the organs or they may become embedded in the intestinal wall. When the devices fall into the intestine, the ends of the wires may become embedded in the wall of the intestine and may become permanently attached, thereby creating an intestinal occlusion. The consequences of such an occlusion may be fatal.

Furthermore, an anastomosis made with that technique does not make it possible to create a long-lasting opening between the stomach and the small intestine. The anastomosis that is created re-closes, since the tissues that are formed are of fibrotic origin.

In the devices described in documents EP 1 790 297 and WO 03/000142, the compression force depends on the thickness of the held-together gastric and intestinal walls, since the compression force provided by the petals at the outer periphery of said devices is uniform.

Necrosis thus matures quickly if the walls are thick. However, necrosis matures more slowly if the walls are thinner.

This observation implies that that type of anastomosis device is not designed to be removed in reliable manner from any patient. Specifically, if the device is put in a patient having gastric and intestinal walls that are thin, and the gastroenterologist wishes to remove the implant at 90 days, there exists a great risk that during surgery, consisting in removing the anastomosis device in order to release the anastomosis that has been created, necrosis is not mature and the surgeon is unable to remove said device. If the same device is put in a patient having gastric and intestinal walls that are thicker in combination, and the gastroenterologist wishes to remove the implant also at 90 days, there thus exists a risk that necrosis has already matured and that the device has fallen into the digestive system.

Another drawback of such anastomosis devices is that they change length little when they pass from their rest and thus deployed position to their compressed position in an insertion catheter. As described below in the present text, the comparative change in length measured on the anastomosis device between its rest position and position forced into an insertion catheter, lies in the range 20% to 70%. Furthermore, in their compressed position in said insertion catheter, the devices measure only 2 centimeters (cm) or 3 cm, which gives the gastroenterologist only very little margin for maneuver when the device leaves the insertion catheter so as to be put into place on the anatomic walls that are to be brought together.

Those devices thus cannot be put into place on the implantation site in a manner that is accurate, reliable, and reproducible.

The anastomosis device of the present invention makes it possible to control necrosis of the combined anatomic walls, such that the surgeon can remove the implant at 90 days of implantation, and such that necrosis is mature.

Furthermore, the anastomosis device of the present invention makes it possible to secure the gastro-intestinal connection immediately after implantation. Said device is then removed after a determined implantation period, which may be about 90 days, so as to enable the intestinal mucosa go back into place, and so as to leave a long-lasting anastomosis in place.

Document WO 2012/175847 A1 discloses an anastomosis device comprising a knitted main tubular body having top and bottom ends that are folded over in such as manner as to form two bearing surfaces that come to pinch together the anatomic walls that are to be brought together.

That type of device does not enable the compression that is exerted on the anatomic walls that are to be brought together and necrotized to be controlled accurately and differently such that, like the above-described prior-art devices, necrosis is not properly controlled. Thus, there exists a risk of the device falling into the digestive system, leading to the above-mentioned problems.

OBJECT AND SUMMARY OF THE INVENTION

The present invention provides an anastomosis device for joining together hollow lumens or viscera, the device being suitable for being deployed at the surface of two superposed adjacent lumens, in particular for the digestive anastomosis, in particular between the stomach and the small intestine, said implantable device comprising a main tubular body of longitudinal axis L, having first and second open ends and opposite inside and outside faces.

Said main tubular body comprises at least three columns of loops and at least three rows of loops.

Advantageously, the tubular body further comprises sets of proximal and distal radial projections extending from said tubular body along at least a depth E at the peripheries of said first and second ends respectively, said distal and proximal sets being spaced apart by a minimum internal distance D.

Said device further comprises a set of intermediate radial projections extending from said body along at most a depth e and arranged between the sets of proximal and distal radial projections, the depth e is less than the depth E, furthermore the minimum internal distance D is determined so as to receive superposed adjacent lumens, in particular the minimum internal distance D is greater than or equal to the sum of the thicknesses of the superposed adjacent lumens.

The proximal, distal, and intermediate sets comprise proximal, distal, and intermediate radial projections respectively.

The depths e and E are defined as being the distances between the point of a radial projection that is farthest from the center of the tubular body, e.g. for a petal the tip of said petal, and the plane containing two adjacent columns of stitches between which said radial projection extends, the distance being measured along a direction that is perpendicular to the plane and that passes via said point.

The internal distance D is the minimum distance between a distal radial projection and a proximal radial projection.

The proximal and distal sets of radial projections do not have the function of exerting a compression effect, but rather they have the function of making it possible to secure the connection between the two superposed adjacent lumens, such as the gastric wall and the intestinal wall, immediately after the anastomosis device has been implanted. The internal distance D between the radial projections of the distal and proximal sets is substantially equal to or greater than the combined thickness of the gastric and intestinal walls, so as to avoid compressing them. Advantageously, this arrangement also makes it possible to keep the anastomosis device connected to the walls of the stomach and of the small intestine until the device is removed, e.g. after 90 days or at 120 days or more of implantation.

The radial projections of the intermediate set guarantee compression of the tissues, thereby enabling their necrosis. The intermediate radial projections do not pinch the anatomic walls that are to be brought together, but exert compression across their thickness.

Advantageously, the depth e of the intermediate radial projections, that is less than the depth E of the distal and proximal radial projections, combined with their arrangement between the distal and proximal radial projections, promote ischemic necrosis of the tissues oriented in a direction that is substantially perpendicular to the longitudinal axis L, also referred to herein below as "radial necrosis", with this applying over a depth e that is less than E. This arrangement makes it easier to remove the anastomosis device at more than 90 days, and in particular at more than 120 days, and further avoids the device falling into the small intestine.

Furthermore, the succession of non-interwoven intermediate radial projections guarantees a compression force that is constant and independent of the thickness of the gastric and intestinal walls. Advantageously, this arrangement makes it possible to control the appearance of necrosis and its maturation time.

Preferably, the anastomosis device of the invention is for implanting and removing by transesophageal endoscopy, without incision by laparotomy.

The first duration of 90 days corresponds to the necrosis maturation time that may be defined as the minimum compression time necessary to necrotize the tissues of the gastric and intestinal walls by ischemia, and then to enable the necrotic tissues to be separated easily from the healthy vascularized portion.

The force for separating the anastomosis device of the invention easily from the site of the anastomosis by gastro-esophageal endoscopy is preferably less than 10 newtons (N).

In the range 90 days to 120 days of implantation, the anastomosis device of the invention cannot fall into the small intestine despite maturation of the necrosis, since it is retained by the proximal and distal radial projections that necrotize tissues very little, if at all.

Preferably, the transesophageal endoscopy uses a dual-channel endoscope of the Olympus GIF 2T160 type that has one working channel with an inside diameter of 2.8 millimeters (mm), and another working channel with an inside diameter of 3.7 mm.

The main tubular body of the invention is preferably made by the weft tubular knitting technique or in other words by the weft-stitch tubular knitting technique.

It is also possible to form the main tubular body manually by forming columns and rows of loops with a wire, e.g. by using a nailed support. In the meaning of the present invention the term "loops" means any stitch loops forming a structural unit of a wire segment having a head, two wings or legs, and two feet, the head being the top portion of the stitch forming a semi-circle, the two wings or legs forming the narrow portion of the stitch connecting the head to the feet, and the two feet being the curved bottom portions of the stitch.

Preferably, said stitch loops are weft stitches, in particular the curved bottom portions or the feet of the stitch loop are incorporated half way along a sinker loop.

Preferably, the main tubular body comprises columns and rows of loops that are formed by means of one or more monofilaments and/or a plurality of multifilament wires, preferably one or more monofilament wires, in particular of a super-elastic alloy, such as an alloy comprising titanium and nickel, preferably in equal proportions by weight.

A super-elastic titanium and nickel alloy is characterized, in part, by its austenite finish temperature, commonly referred to as Af. It corresponds to the temperature at the end of the change of phase between the martensite phase and the austenite phase. In its martensite phase, the titanium and nickel alloy is malleable, and in its austenite phase the alloy is very elastic. In the range of temperatures in which the austenite phase is stable, i.e. for a temperature that is greater than or equal to Af, transformation to martensite may also be caused by applying stress. Superplasticity is thus characterized by immediate and complete recovery of the wire when the applied stress ceases. The stress then acts in the elastic deformation range of the austenite. The temperature Af characterizing the transition of the super-elastic wire of the present invention lies in the range −10° C. to 5° C., and makes it possible to have the desired super-elastic behavior. A shape-memory wire may be defined by a temperature Af that is higher than 5° C. This "shape-memory" wire is not suitable in the context of the present invention since the radial compression force of the anastomosis device is not sufficient.

Preferably, said monofilament wire(s) have a diameter lying in the range 0.15 mm to 0.35 mm, more preferably in the range 0.2 mm to 0.25 mm.

Preferably, said multifilament wire(s) have a size that lies in the range 114 tex to 620 tex for a number of filaments per wire lying in the range 2 to 10.

In a variant embodiment, the radial projections are formed by segments that connect the columns of loops, said columns of loops having a longitudinal axis l that is substantially parallel to the longitudinal axis L of the tubular body.

The segments that connect the columns of loops are preferably formed out of a monofilament or multifilament wire, and more preferably out of a monofilament wire, such as a super-elastic alloy, in particular made of titanium-nickel, preferably in equal proportions by weight, and more preferably substantially 50% of titanium for 50% of nickel by weight relative to the total weight of the wire.

In a variant embodiment, each set of radial projections, whether it be distal, proximal, or intermediate, comprises at least two rows of loops, each row comprising radial projections, said radial projections being arranged in planes (p), said planes (p) intersecting the longitudinal axis L.

In a sub-variant, the radial projections of the proximal and distal sets are arranged in planes (p) that are substantially parallel to one another and perpendicular to the longitudinal axis L.

In a sub-variant, the radial projections of the intermediate set are in planes (p) that are substantially perpendicular to the longitudinal axis L when the device is at rest, i.e. in a deployed position, and in planes (p) that form an angle β, lying in the range 10° C. to 85° C., with the longitudinal axis L in operation, i.e. when radial compression is exerted on said intermediate projections. In a variant embodiment, the radial projections of two adjacent rows of loops are spaced apart by a distance d that corresponds substantially to the height of a loop.

These various arrangements make it possible to better control the compression exerted by each of the projections, since said projections are not interwoven unlike the anastomosis devices in the prior art.

In a variant embodiment, the radial projections of the distal and/or proximal set(s), and possibly the radial projections of the intermediate set, have the shape of petals, in particular a shape that is selected, independently from one projection to another, from among the following shapes: a circular arc, a semi-circular shape, a semi-elliptical shape, and a parabolic shape.

The particular configuration of the main tubular body of the invention and the arrangement of the rows and columns of loops enable multiple shapes to be used for the radial projections, since said radial projections are independent from one another.

In a variant embodiment, the depth E is greater than or equal to twice the depth e, preferably greater than or equal to three times, more preferably greater than or equal to five times, and still more preferably greater than or equal to eight times the depth e.

In a variant embodiment, the main tubular body presents longitudinal elongation along axis L that is greater than or equal to 200% to within ±20%, preferably greater than or equal to 380% to within ±20%.

This arrangement enables the anastomosis device of the invention to elongate in significant manner so as to pass into a catheter of inside diameter not less than 3.0 mm.

The percentage of axial elongation of the anastomosis device between its deployed position, i.e. at rest before its implantation, and its compressed position inside a catheter with an inside diameter of 3.0 mm lies in the range 380% to 520% to within ±20%.

This elongation is measured by comparing the elongation of the anastomosis device at rest with the elongation obtained after forcing it into an insertion catheter having an inside diameter of 3.0 mm for an outside diameter of 3.50 mm, in particular a catheter made out of polymer of polyether block amide (PEBA), its inside duct being coated with a fluorinated polymer, in particular with a polytetrafluoroethylene (PTFE) film having thickness of about 50 micrometers (μm).

This elongation enables high accuracy in positioning the device of the invention by transesophageal endoscopy.

This large elongation is obtained by the combination of the rows of loops and of the columns of loops, preferably formed by knitting, in particular by the formation of weft stitches, with the use of a wire made out of a titanium-nickel super-elastic alloy.

This arrangement enables the operating technique to be very reproducible.

In a variant embodiment, the main tubular body comprises five to ten columns of loops, and three to six radial projections per row of loops.

Thus, as a function of the number of columns of loops, it is possible to adjust the number of radial projections per row of loops, the number of radial projections being less than or equal to the number of columns of loops.

Specifically, in the manufacturing method used for the main tubular body, it is possible to provide a number of radial projections per row of loops that is less than the number of available segments on a row of loops, i.e. thus less than the number of available columns of loops.

The inventors have determined that this arrangement provides a compromise between the compression force that is sufficient to create ischemic necrosis, the formation of an immediate connection with the walls of the stomach and of the small intestine, and occupying a minimum amount of space, making it possible to optimize the elongation of the anastomosis device inside the insertion catheter.

In a variant embodiment, the main tubular body includes one to ten radial projections arranged between two adjacent columns of loops, said projections belonging to the distal and proximal and/or intermediate sets.

In a variant embodiment, each of the sets of distal and proximal radial projections comprises at least two rows of loops, and when the set of intermediate radial projections comprises three to eight rows of loops, said rows comprise three to eight radial projections.

In a variant, the minimum distance D lies in the range 4 mm to 20 mm, preferably in the range 6 mm to 16 mm. In a variant embodiment, the main tubular body has an inside diameter a lying in the range 10 mm to 30 mm, preferably in the range 10 mm to 25 mm, and more preferably in the range 20 mm to 25 mm.

In a variant embodiment, the columns and the rows of loops of the main tubular body are formed from one or more monofilament wires and/or one or more multifilament wires made out of a super-elastic titanium-nickel alloy.

DETAILED DESCRIPTION OF THE INVENTION

Figure 1:
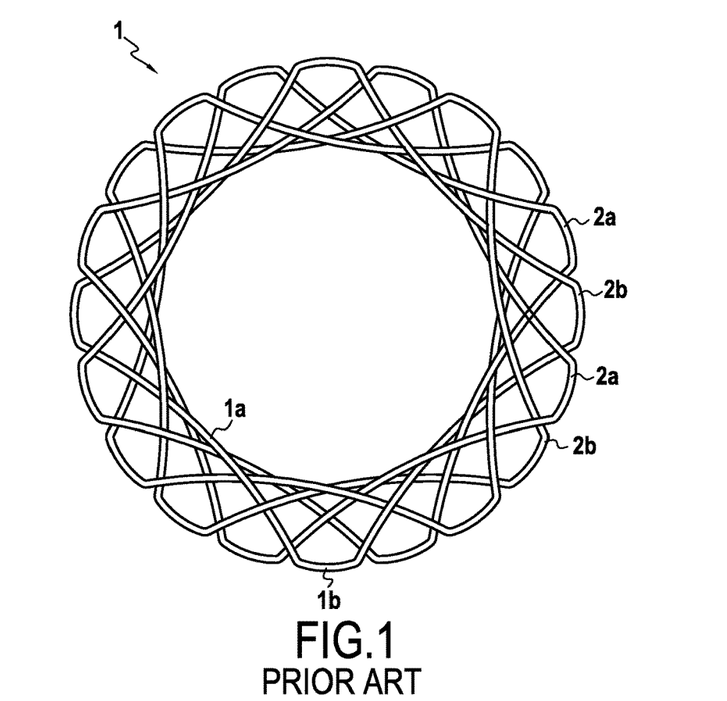
FIG. 1 is a diagrammatic representation in plan view of a first embodiment of an anastomosis device of the prior art.

The first example of an anastomosis device 1 of the prior art comprises an inner periphery is and an outer periphery 1b and bottom and top petals 2b, 2a.

The device 1 is suitable for necrotizing tissues. When tissues necrotize over time, the device 1 may be separated from the healthy tissues on the site of the anastomosis, and may thus pass through the digestive system of the patient.

The device 1 corresponds to FIG. 3A in document EP 1 790 297 A1.

The inner periphery is corresponds to the portion of the tube from which the device 1 has been formed by folding over, and the top and bottom ends of the open tube that have been brought together correspond to the outer periphery 1b.

Figure 2:
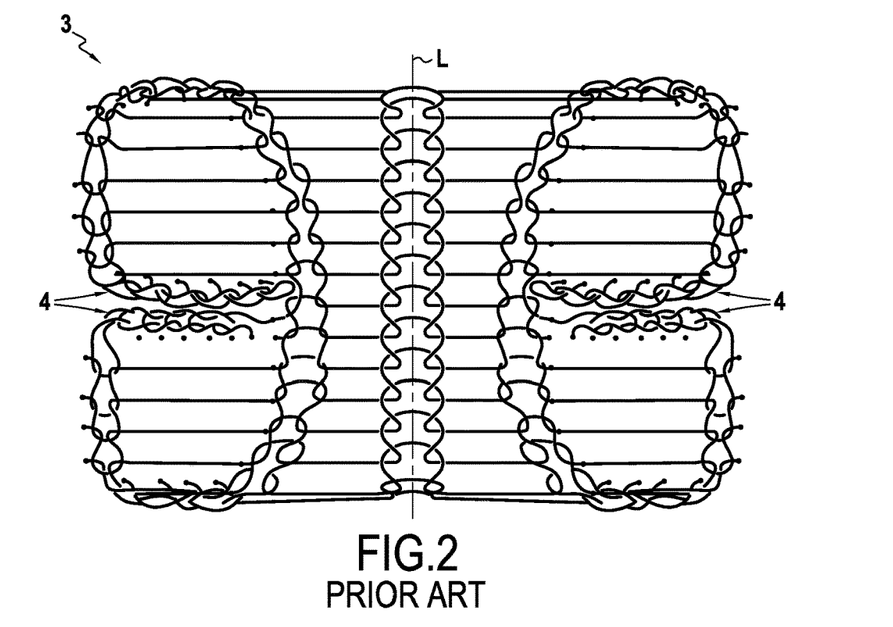
FIG. 2 is a diagrammatic representation in perspective and in side view of a second embodiment of an anastomosis device of the prior art.

The anastomosis device 3 shown in FIG. 2 is a second example of a device of the prior art and includes bearing faces 4 that are oriented to face each other, and that come to pinch the walls of the stomach and the small intestine together.

Figure 3:
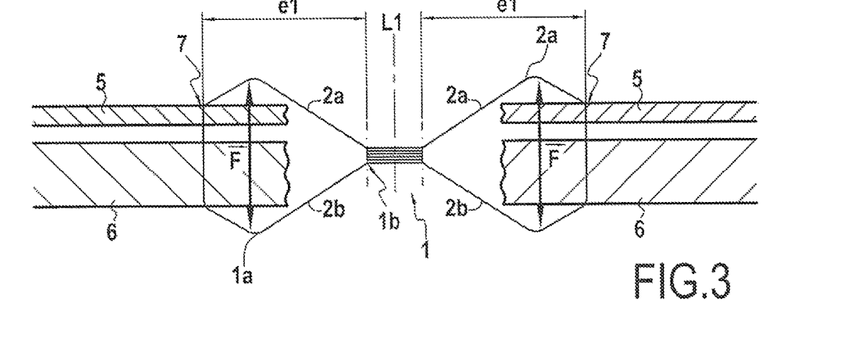
FIG. 3 is a diagrammatic side view of the behavior of an anastomosis device of the prior art, such as the device shown in FIG. 1, on the site of the anastomosis, while holding the walls of the stomach and of the small intestine compressed together, when combined thickness of the gastric and visceral walls is large.

FIG. 3 shows the anastomosis device 1 in operation, i.e. in a position in which it is deployed and holds together the anatomic walls 5 and 6 that correspond to the intestinal wall and the gastric wall respectively.

It should be observed that the depth of the top and bottom petals 2a, 2b is the same, and corresponds substantially to the thickness e1 measured from the longitudinal axis L1 of the device 1.

The outer periphery is of the device 1 thus necrotizes the superposed portions of the walls 5 and 6 at the annular zones 7.

Once necrosis has ended, the device 1 falls into the digestive system of the patient causing the above-mentioned risks.

The device described in FIG. 2 behaves in the same manner with the bearing faces 4 facing each other.

Figure 4A:
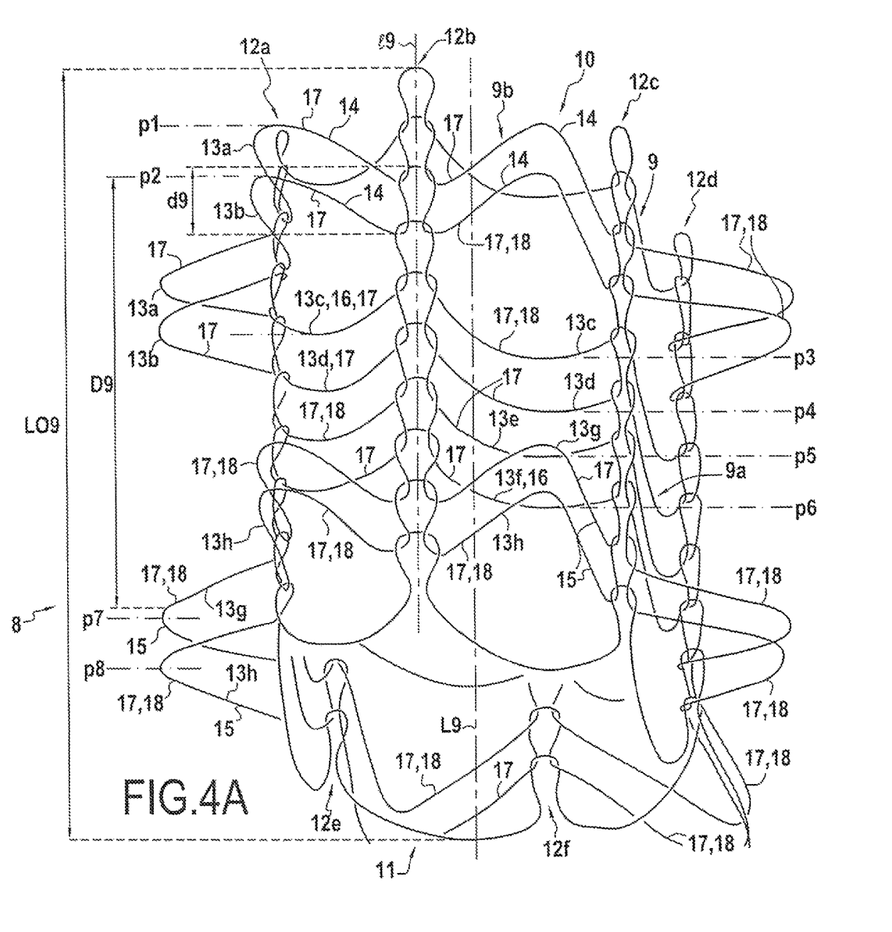
FIG. 4A is a diagrammatic representation in perspective of a first embodiment of an anastomosis device of the invention.

The first embodiment of an anastomosis device 8 of the invention, shown in FIG. 4A, for joining hollow lumens or viscera, in this specific embodiment the walls of the stomach 20 and of the small intestine 19, comprises a main tubular body 9 of longitudinal axis $L_9$, having first and second open ends 10, 11, and opposite outside and inside faces 9a, 9b. In this specific embodiment, said main tubular body 9 comprises six columns of loops 12a to 12f and eight rows of loops 13a to 13h.

The main tubular body 9 comprises sets of proximal and distal radial projections 14, 15 that extend from said tubular body 9 along a depth $E_9$ at the periphery of said first and second open ends 10, 11 respectively. Said distal and proximal sets 15, 14 are spaced apart by a minimum internal distance $D_9$.

The main tubular body 9 further comprises a set of intermediate radial projections 16 that extend from said tubular body 9 along a depth $e_9$, and that are arranged between the sets of proximal and distal radial projections 14, 15. The depth $e_9$ is less than $E_9$.

Furthermore, the minimum internal distance $D_9$ is determined so as to receive superposed adjacent lumens, namely the anatomic walls that are to be brought together, specifically the intestinal wall 19 and the gastric wall 20, $D_9$ is determined so as to be greater than or equal to the sum of the thicknesses of the intestinal and gastric walls 19, 20.

The radial projections 17 are formed by segments 18 that connect the columns of loops 12a to 12f, which columns of loops 12a to 12f have a longitudinal axis $l_9$ that is substantially parallel to the longitudinal axis $L_9$ of the tubular body 9.

In this specific embodiment, each of the sets of radial projections 17, both proximal and distal projections 14, 15, comprises two rows of loops, namely the rows of loops 13a & 13b and 13g & 13h respectively, said radial projections 17 of each row 13a, 13b, 13g, 13h are arranged in substantially-parallel planes p1, p2 and p7, p8, said planes p1, p2 and p7, p8 intersecting the longitudinal axis $L_9$, in particular both at rest and in operation, substantially perpendicularly to the longitudinal axis $L_9$.

In this specific embodiment, the set of intermediate radial projections 16 comprises four rows of loops 13c, 13d, 13e, 13f, each row 13c to 13f comprises radial projections 17, which radial projections 17 of each row 13c to 13f are arranged in planes p3, p4, p5, p6 respectively, said planes p3, p4, p5, p6 form an angle β9 that lies in the range 10° to 85° with the longitudinal axis $L_9$.

The radial projections 17 of two adjacent rows of loops, e.g. 13a and 13b, are spaced apart by a distance $d_9$ that corresponds substantially to the height of a loop.

In this specific embodiment, the radial projections 17 of the distal, proximal, and intermediate sets 15, 14, 16 have the shape of a petal.

The depth $E_9$ is greater than or equal to four times the depth $e_9$, in this specific embodiment $E_9$ is equal to five times the depth $e_9$.

The main tubular body 9 includes eight radial projections arranged between two adjacent columns of loops, such as columns 12a and 12b for example, said projections 17 belonging to the proximal, distal, and intermediate sets 14, 15, 16.

In this specific embodiment, the inside diameter $a_9$ is about 25 mm, the minimum distance $D_9$ between the first radial projection 17 of the proximal and distal sets 14, 15 is about 10 mm, finally the length $L_9$ at rest of the tubular body 9 of the device 8 is about 20 mm.

The percentage of axial elongation of the device 8 is about 400% to within ±20%.

The elongation is measured on the anastomosis device 8, and occurs as a result of putting the device 8 into a catheter of small inside diameter of about 3.0 mm, for an outside diameter of 3.50 mm.

The catheter is made of polyether block amide (PEBA) and presents an inside surface that is coated with a fluorinated polymer, in particular polytetrafluorethylene, such as Teflon, having thickness of about 50 μm.

Forcing the entire anastomosis device 8 into such a catheter causes it to elongate, giving its elongation in the compressed state $L_{c9}$.

An elongation difference is thus obtained between the length $L_9$ at rest of the anastomosis device, of about 2 cm, and a length $L_{c9}$ in a compressed state of about 10 cm, corresponding to a latitude in placement $L_{a9}$ of about 8 cm, available to the surgeon when the anastomosis device 8 comes out of the inserter at the implantation site.

The length in the compressed state of the device 8 is measured by means of a graduated ruler through the thickness of the wall of the insertion catheter.

By way of comparison, the anastomosis device 1 shown in FIG. 1 has a length L1 at rest of about 2 cm, and a length LC1 in the compressed state inside said insertion catheter of about 3.4 cm, which represents a latitude in placement of about 1.4 cm and an elongation of 70%.

It should thus be clearly understood that the anastomosis device 8 of the invention offers the practitioner more freedom and reliability in its positioning at the anatomic walls 19 and 20 that are to held and necrotized. The very small elongation of the anastomosis devices of the prior art generates a risk that such a device, when it is deployed at the implantation site on leaving the inserter, will be released too quickly since it can be held over only a very small length, and as a result it can fall directly into the patient's digestive system.

The inside diameter of the device 1 is also about 25 mm.

In this embodiment, this is the inside diameter of the tube from which the device 1 is shaped, and in particular the inner periphery is of the device 1.

In this specific embodiment, the tubular body 9 is preferably manufactured with a weft tubular knitting technique or by a weft-stitch tubular knitting technique with a monofilament wire with an outside diameter 0.25 mm, preferably made of a shape-memory alloy based on titanium and nickel, and more preferably in a super-elastic alloy.

As can be seen in FIG. 4A, each loop presents a head, legs, wings, and feet of a stitch.

The loops of the columns and of the rows are the same, and they are situated at the intersections of the columns 12a to 12f and of the rows 13a to 13h.

Figure 4B:
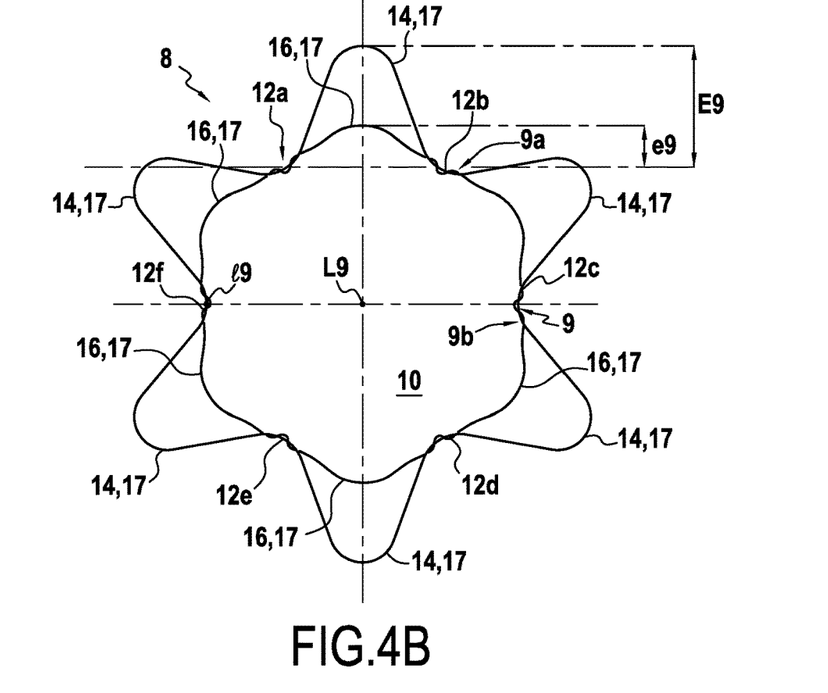
FIG. 4B is a diagrammatic representation in plan view of the anastomosis device shown in FIG. 4A.

FIG. 4B is a plan view of the anastomosis device 8, and the depth $e_9$ corresponds to the depth of the radial projections 17 of the intermediate set 16.

Figure 5:
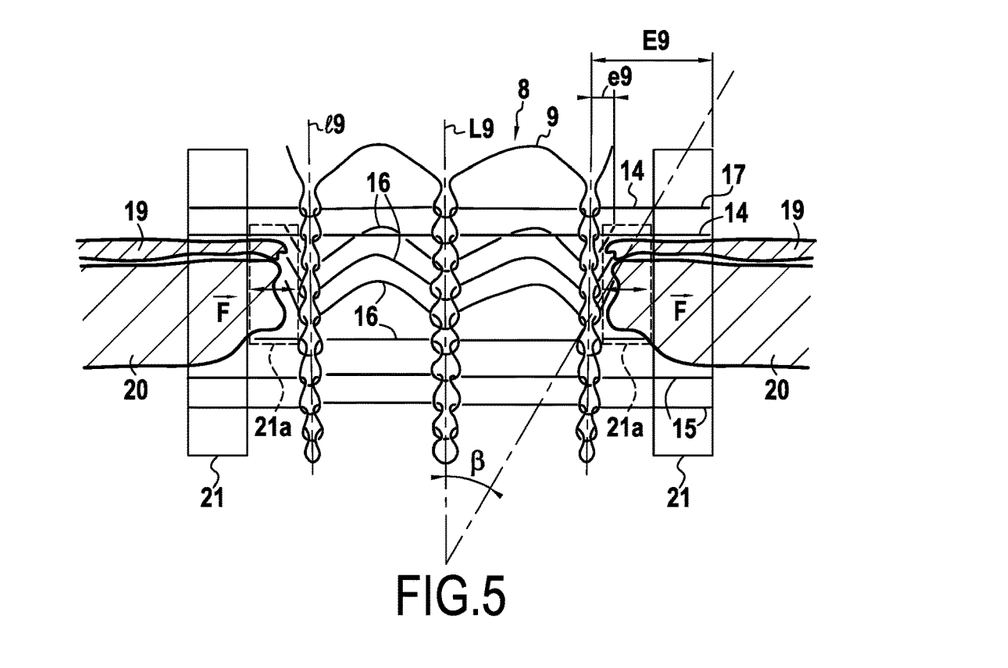
FIG. 5 is a diagrammatic representation of the anastomosis device shown in FIGS. 4A and 4B on the site of the anastomosis.

FIG. 5 shows the anastomosis device 8 on the implantation site in a position in which it holds the intestinal wall 19 and the gastric wall 20 together.

It should thus be observed that the radial projections 17 of the proximal and distal sets 14, 15 hold the intestinal and gastric walls 19, 20 together, without exerting compression force. The radial projections 17 of the intermediate set 16 exert a compression effect against the anatomic walls 19 and 20.

The compression effect is exerted along arrows f for each of the radial projections 17, in this embodiment the compression effect is exerted along a direction f that is substantially perpendicular to the axis L9 of the tubular body 9, such that the intestinal and gastric walls 19, 20 are not necrotized over the entire zone 21, in particular over the entire thickness of the tissues 19, 20 in the axial direction (corresponding to L9). In particular, the tissues 19, 20 are necrotized over the zones 21a corresponding to the depth $e_9$ of the intermediate 16 radial projections 17.

The sets of distal 15 and proximal 14 radial projections 17 make it possible to hold the anatomic walls 19 and 20 together without exerting a compression effect, so as to secure the anatomic connection in the first moments after implantation via transesophageal approach, while the radial projections 17 of the intermediate set 16 exert a compression effect that is oriented mainly along the arrows f, in a direction that is substantially perpendicular to the longitudinal axis L9 of the anastomosis device 9, thereby making it possible to create necrosis that is preferably radial, and thereby making it easier to remove the device at the end of 90 days, or at 120 days.

Advantageously, the sets of distal 15 and proximal 14 radial projections 17 also make it possible to hold the anastomosis device on the anatomic walls 19 and 20, even when necrosis reaches maturity.

The necrosis obtained with the anastomosis device 8 is radial necrosis, unlike the axial necroses obtained in the prior art, and this makes it easier to remove the device at 90 days or up to 120 days, and avoids the device falling into the patient's digestive system, and in particular detaching from the anatomic walls 19 and 20, which means that it needs to be removed by the surgeon.

Figure 6:
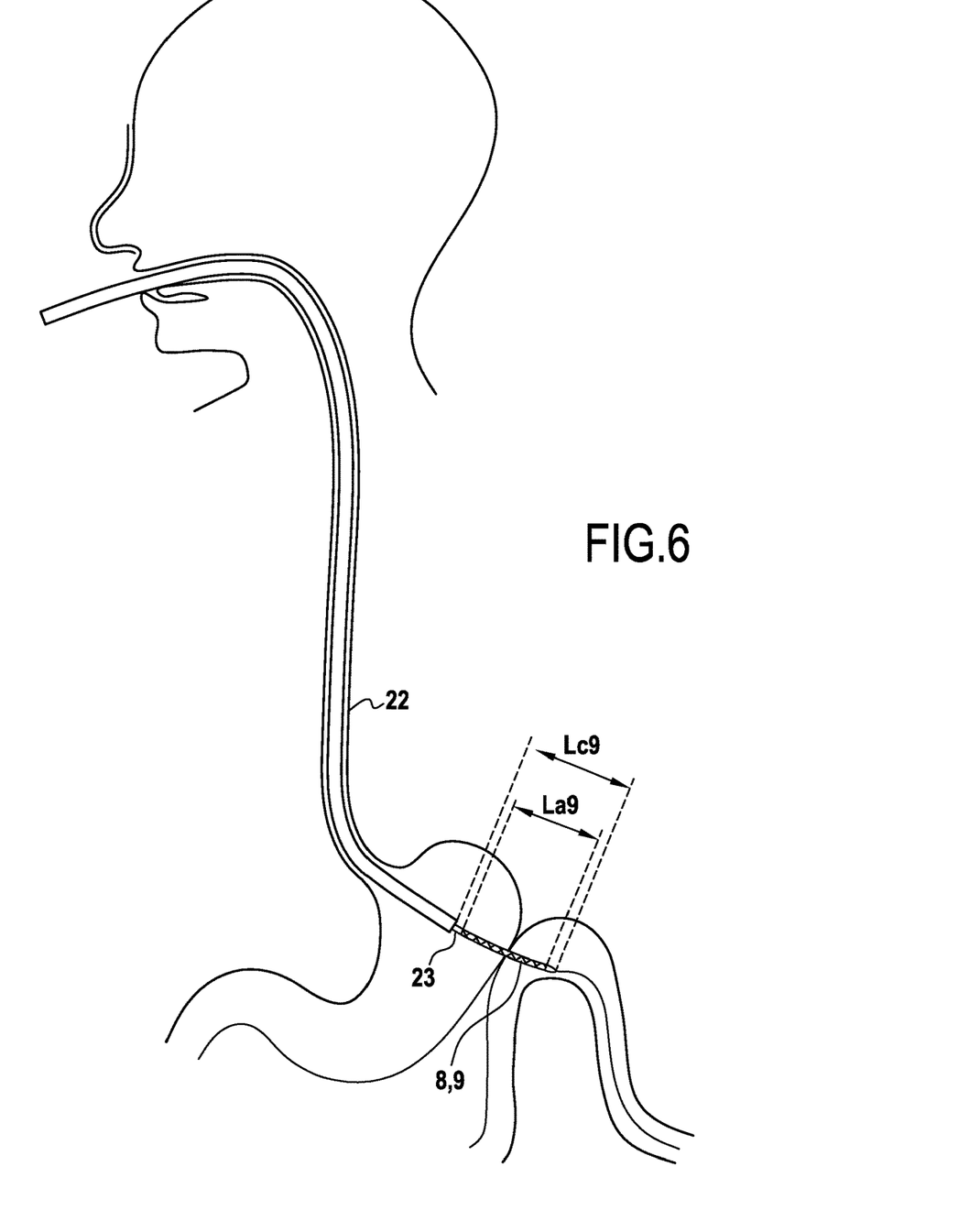
FIG. 6 is a diagrammatic view in perspective of the positioning of the anastomosis device shown in FIGS. 4A, 4B, and 5 on the implantation site via transesophageal approach by means of an endoscope using an insertion catheter with an inside diameter of 3.0 mm.

FIG. 6 is a diagram showing the arrangement of the device 8 on the anastomosis site. It can thus be seen that while removing the device 9 from the endoscope 22, and in particular from the catheter 23, the practitioner has latitude in placement La9 of about 8 cm, which makes it possible to position the radial projections of the distal and proximal sets 14, 15 correctly, without any risk of said device 9 falling into the patient's digestive system.

Figure 7:
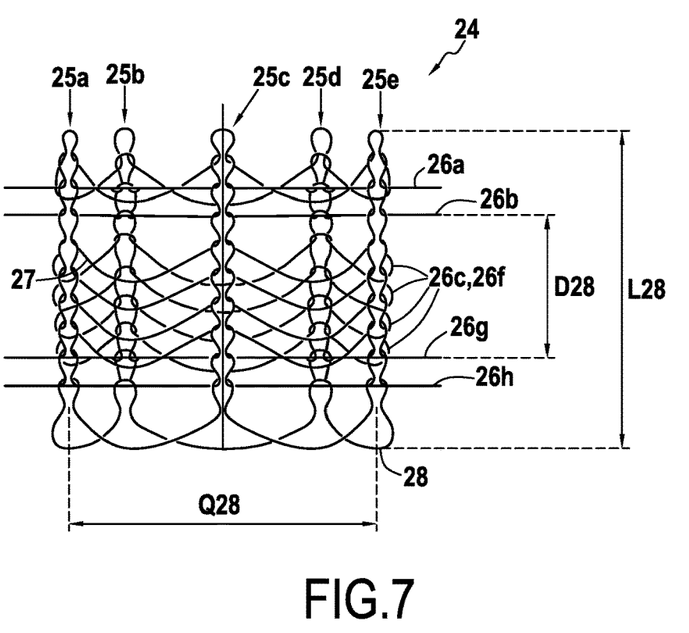
FIG. 7 is a diagrammatic representation in perspective of a second embodiment of an anastomosis device of the invention.
Figure 8:
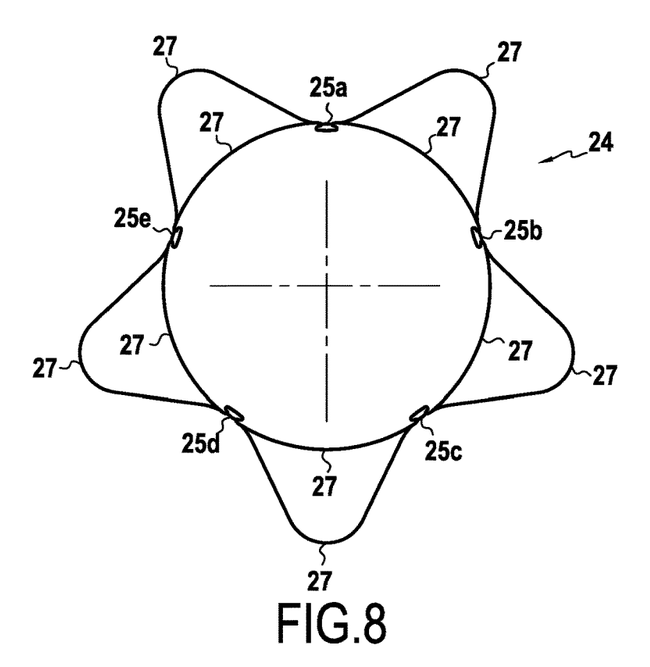
FIG. 8 is a diagrammatic representation in plan view of the anastomosis device shown in FIG. 7.

The second embodiment of an anastomosis device 24 of the present invention is shown in FIGS. 7 and 8 and comprises five columns of loops 25a, 25b, 25c, 25d, 25e and eight rows of loops 26a to 26h.

The anastomosis device 24 differs from the anastomosis device 9 by the number of columns of loops.

In this embodiment, the arrangement of the radial projections 27 is the same as the radial projections 17.

The reduction in the number of columns of loops makes it possible to reduce the space occupied by the anastomosis device 24 for an inside diameter a28 of the tubular body 28 of about 25 mm, i.e. of the same order as a9, and makes it possible to obtain greater latitude in placement La28, namely about 10 cm.

Specifically, in this embodiment, the elongation obtained by means of an insertion catheter for the anastomosis device 24 is about 500%, ±20%, measured in the same way as described above.

In this embodiment, the minimum distance D28 is about 7 mm, the length L28 of the tubular body 28 is about 20 mm, and the length LC28 in the compressed state of the device 24 is about 120 mm.

What is claimed is:

1. An anastomosis device for joining together hollow lumens or viscera, the device being suitable for being deployed at the surface of two superposed adjacent lumens, said device comprising:
   a main tubular body of longitudinal axis (L), having first and second open ends and opposite outside and inside faces, said main tubular body comprising at least three columns of loops and at least three rows of loops that are formed of one or more monofilament wires and/or one or more multifilament wires,
   wherein said tubular body further comprises sets of proximal and distal radial projections extending from said tubular body along at least a depth (E) at the peripheries of said first and second ends respectively, said distal and proximal sets being spaced apart by a minimum internal distance (D),
   wherein it further comprises a set of intermediate radial projections extending from said body along at most a depth (e) and arranged between the sets of proximal and distal radial projections, wherein (e) is less than (E), and
   wherein the minimum internal distance (D) is determined so as to receive two superposed adjacent lumens.

2. The anastomosis device according to claim 1, wherein the radial projections are formed by segments that connect the columns of loops, which columns of loops have a longitudinal axis (1) that is substantially parallel to the longitudinal axis (L) of the tubular body.

3. The anastomosis device according to claim 1, wherein each set of radial projections comprises at least two rows of loops, said radial projections being arranged in planes (p), said planes (p) intersecting the longitudinal axis (L).

4. The anastomosis device according to claim 1, wherein the radial projections of the proximal and distal sets are arranged in planes (p) that are substantially parallel to one another and perpendicular to the longitudinal axis L.

5. The anastomosis device according to claim 1, wherein the radial projections of the intermediate set are in planes (p) that are substantially perpendicular to the longitudinal axis L when the device is in a deployed position, and in planes (p) that form an angle β, lying in the range 10° to 85°, with the longitudinal axis L when radial compression is exerted on said intermediate projections.

6. The anastomosis device according to claim 1, wherein each set of radial projections comprises at least two rows of loops, the radial projections of two adjacent rows of loops being spaced apart by a distance (d) that corresponds substantially to the height of a loop.

7. The anastomosis device according to claim 1, wherein the radial projections of the distal and/or proximal set(s) and/or the radial projections of the intermediate set, have the shape of petals, in particular a shape that is selected, independently from one projection to another, from among the following shapes: a circular arc, a semi-circular shape, a semi-elliptical shape, and a parabolic shape.

8. The anastomosis device according to claim 1, wherein the depth (E) is greater than or equal to twice the depth (e).

9. The anastomosis device according to claim 8, wherein the depth (E) is greater than or equal to eight times the depth (e).

10. The anastomosis device according to claim 1, wherein the main tubular body presents longitudinal elongation along axis (L) that is greater than or equal to 200% to within ±20%.

11. The anastomosis device according to claim 10, wherein the main tubular body presents longitudinal elongation along axis (L) that is greater than or equal to 380% to within ±20%.

12. The anastomosis device according to claim 1, wherein the tubular body comprises five to ten columns of loops, and three to six radial projections per row of loops.

13. The anastomosis device according to claim 1, wherein the main tubular body includes one to ten radial projections arranged between two adjacent columns of loops, said projections belonging to the distal and/or proximal and/or intermediate set(s).

14. The anastomosis device according to claim 1, wherein each of the sets of distal and proximal radial projections comprises at least two rows of loops, and wherein the set of intermediate radial projections comprises three to eight rows of loops, said rows comprising three to eight radial projections.

15. The anastomosis device according to claim 1, wherein the minimum distance (D) lies in the range 4 mm to 20 mm.

16. The anastomosis device according to claim 1, wherein the main tubular body has an inside diameter (a) lying in the range 10 mm to 30 mm.

17. The anastomosis device according to claim 1, wherein the columns and the rows of loops are formed from one or more monofilament wires and/or one or more multifilament wires made out of a super-elastic titanium-nickel alloy.

18. An anastomosis device for joining together hollow lumens or viscera, the device being suitable for being deployed at the surface of two superposed adjacent lumens, said device comprising:
   a main tubular body of longitudinal axis (L), having first and second open ends and opposite outside and inside faces, said main tubular body comprising at least three columns of loops and at least three rows of loops, wherein said tubular body further comprises sets of proximal and distal radial projections extending from said tubular body along at least a depth (E) at the peripheries of said first and second ends respectively, said distal and proximal sets being spaced apart by a minimum internal distance (D), wherein said tubular body further comprises a set of intermediate radial projections extending from said body along at most a depth (e) and arranged between the sets of proximal and distal radial projections, wherein (e) is less than (E), and wherein the minimum internal distance (D) is determined so as to receive two superposed adjacent lumens and wherein the radial projections are formed by segments that connect the columns of loops, which columns of loops have a longitudinal axis (l) that is substantially parallel to the longitudinal axis (L) of the tubular body.

19. An anastomosis device for joining together hollow lumens or viscera, the device being suitable for being deployed at the surface of two superposed adjacent lumens, said device comprising:

a main tubular body of longitudinal axis (L), having first and second open ends and opposite outside and inside faces, said main tubular body comprising at least three columns of loops and at least three rows of loops, wherein said tubular body further comprises sets of proximal and distal radial projections extending from said tubular body along at least a depth (E) at the peripheries of said first and second ends respectively, said distal and proximal sets being spaced apart by a minimum internal distance (D), wherein said tubular body further comprises a set of intermediate radial projections extending from said body along at most a depth (e) and arranged between the sets of proximal and distal radial projections, wherein (e) is less than (E), wherein the minimum internal distance (D) is determined so as to receive two superposed adjacent lumens, and wherein each set of radial projections comprises at least two rows of loops, said radial projections being arranged in planes (p), said planes (p) intersecting the longitudinal axis (L).

* * * * *